United States Patent [19]

Regnier et al.

[11] Patent Number: 4,792,559
[45] Date of Patent: Dec. 20, 1988

[54] 1,2,3,4-TETRAHYDROQUINOLINE SUBSTITUTED 5-AMINOPENTANENITRILE COMPOUNDS AND THEIR USE AS CALCIUM MODULATORS

[75] Inventors: Gilbert Regnier, Chatenay Malabry; Yves-Michel Gargouil, Paris; Jean-Paul Vilaine, Le Plessis Robinson, all of France

[73] Assignee: ADIR et Compagnie, Neuilly-sur-Seine, France

[21] Appl. No.: 911,483

[22] Filed: Sep. 25, 1986

[30] Foreign Application Priority Data

Oct. 4, 1985 [FR] France ................... 8514756

[51] Int. Cl.$^4$ .................. C07D 215/26; A61K 31/47
[52] U.S. Cl. ............................. 514/311; 546/165; 546/168; 546/171; 546/172; 546/177; 546/178; 546/179
[58] Field of Search ............... 546/165; 514/311

[56] References Cited

U.S. PATENT DOCUMENTS 3,444,173  5/1969  Goldman ................... 546/165

FOREIGN PATENT DOCUMENTS 0064158  11/1982  European Pat. Off.
2663M    4/1962  France.

OTHER PUBLICATIONS

Index Nominum (1987), p. 1089.

Primary Examiner—Glennon H. Hollrah
Assistant Examiner—D. B. Springer
Attorney, Agent, or Firm—Gordon W. Hueschen

[57] ABSTRACT

5-aminopentanenitrile compounds of the formula:

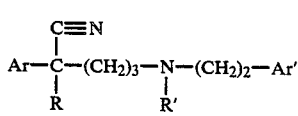

in which:
Ar represents

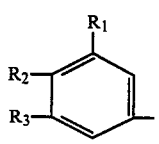

in which:

$R_1$ is hydrogen, halogen trifluoromethyl or $C_1$-$C_5$-alkoxy, and $R_2$ and $R_3$, which are identical or different, each are hydrogen or $C_1$-$C_5$-alkoxy or together form —O—CH=CH—O— or —O—CH$_2$—O—; or together form with the phenyl ring to which they are bound a benzoxazolyl, benzothiazolyl, benzothiadiazolyl or quinolyl radical;

R is $C_3$-$C_{15}$-alkyl or

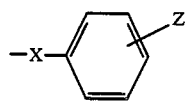

in which:
X is S or SO$_2$ and Z is hydrogen, chlorine or $C_1$-$C_5$-alkyl or $C_1$-$C_5$-alkoxy;
R' is $C_1$-$C_5$-alkyl, and
Ar' represents

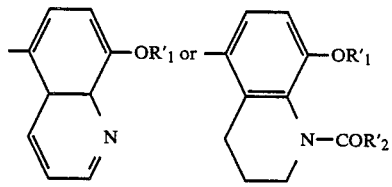

in which:
R'$_1$ is $C_1$-$C_5$-alkyl and
R'$_2$ is hydrogen or $C_1$-$C_4$-alkyl; and moreover when R is

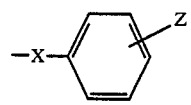

Ar' may be

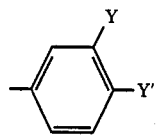

in which
Y is $C_1$-$C_5$ alkoxy and
Y' is hydrogen or $C_1$-$C_5$ alkoxy These compounds (I), and physiologically tolerable acid salts thereof may be used as medicines especially in the treatment of disorders requiring modulators of transmembrane and intracellular movements of calcium.

8 Claims, No Drawings

1,2,3,4-TETRAHYDROQUINOLINE SUBSTITUTED 5-AMINOPENTANENITRILE COMPOUNDS AND THEIR USE AS CALCIUM MODULATORS

The present invention provides 5-aminopentanenitrile compounds of the general formula I:

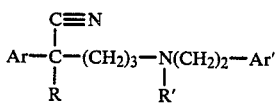  (I)

in which:
Ar represents a radical of the formula:

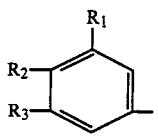

in which:
$R_1$ is selected from the group consisting of hydrogen, halogen, trifluoromethyl and alkoxy containing from 1 to 5 carbon atoms inclusive, and
$R_2$ and $R_3$, which are the same or different, are each selected from the group consisting of hydrogen and alkoxy containing from 1 to 5 carbon atoms inclusive, or
$R_2$ and $R_3$ together represent a radical selected from the group consisting of —O—CH=CH—O— and —O—CH$_2$—O—;

or
$R_2$ and $R_3$ together form with the phenyl radical to which they are bound a radical selected from the group consisting of benzoxazolyl, benzothiazolyl, benzothiadiazolyl and quinolyl.
R is selected from the group consisting of straight-chain and branched alkyl containing from 3 to 15 carbon atoms, and a radical of the formula:

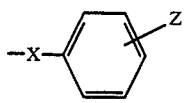

in which:
X is selected from the group consisting of S and SO$_2$ and Z is selected from the group consisting of hydrogen, chlorine and alkyl and alkoxy each having from 1 to 5 carbon atoms inclusive,
R' is selected from the group consisting of alkyl containing from 1 to 5 carbon atoms inclusive, and
Ar' is selected from the group consisting of radicals of the formula:

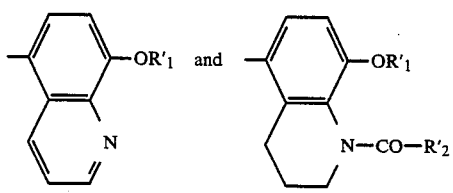

in which:
$R'_1$ is selected from the group consisting of straight-chain and branched alkyl containing from 1 to 5 carbon atoms inclusive, and
$R'_2$ is selected from the group consisting of hydrogen and straight-chain and branched alkyl containing from 1 to 4 carbon atoms inclusive, and, moreover, when R is

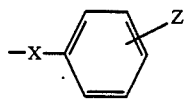

Ar' also represents
a radical of the formula:

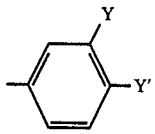

in which:
Y is selected from the group consisting of alkoxy containing from 1 to 5 carbon atoms inclusive, and
Y' is selected from the group consisting of hydrogen and alkoxy containing from 1 to 5 carbon atoms inclusive.

The prior art in this field may be illustrated especially by the French Patent No. 2663 M and the European Patent application No. 0064.158, which relate to phenylacetonitriles of the formula:

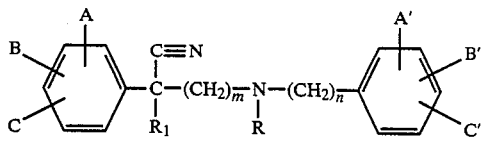

in which:
m and n are integers from 2 to 5,
R and $R_1$ represents, among others a lower alkyl radical or a phenyl radical,
A, B, C, A', B', C' are classic substituents especially hydrogen, halogen, lower alkyl and alkoxy or methylenedioxy.

These phenylacetonitriles, the most representative trade product of which is verapamil, have a spasmolytic activity, increase the coronary irrigation and have a dilating activity on the coronary vessels.

Moreover, it is known that verapamil is a cardiotropic agent having negative inotropic effects and particularly inducing an extension of the PR space of the electro-cardiogram, thus showing a decrease of the auriculo-ventricular conduction and landing, in clinical use, some bad side effects such, for example, as fibrillation.

The products of the present invention, and more especially the compound of example 1 here-after described, do not possess these disadvantages because they differ from verapamil by their pharmacological behaviour, showing a greater affinity for calcium channels (which may be 20 times the one of verapamil), an affinity for calmodulin coherent with the biological effect and a greater selectivity in favour of vessels; thus allowing to regulate arterial hypertension in acting preferentially on vessels rather than on heart muscle so avoiding the bad side effects and particularly the risk of fibrillation.

The present invention also relates to a process for the preparation of compounds of the general formula I, characterised in that a halogenated compound of the general formula II:

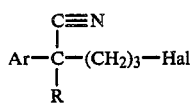
(II)

in which:

Ar and R have the above-mentioned meanings, and Hal represents a halogen atom, such as, for example, a chlorine or bromine atom, is reacted with an amine of the general formula III:

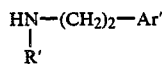
(III)

in which:

R' and Ar' have the meanings defined above.

It is particularly advantageous to carry out this reaction in a suitable solvent, such as, for example, acetonitrile, methyl ethyl ketone and water-miscible alcohols, of low boiling point, the reaction being carried out at a temperature of from 60° to 100° C.

The present invention also relates to a process for the preparation of compounds of the general formula I, characterised in that a compound of the general formula IV:

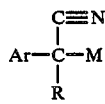
(IV)

in which:

Ar and R have the meanings defined above, and

M represents a sodium or lithium atom, is reacted with a halogenated compounds of the general formula V:

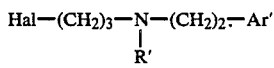
(V)

in which:

R' and Ar' are as defined above, and Hal represents a halogen atom, such as, for example, a chlorine or bromine atom.

It is particularly appropriate to carry out such a reaction in a suitable solvent, such as, for example, tetrahydrofuran or toluene, at a temperature of from 60° to 110° C.

The present invention also includes a process for the preparation of compounds of the general formula I where Ar' represents

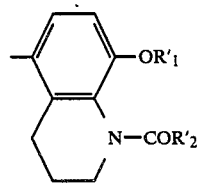

that is to say, the compounds of the general formula I':

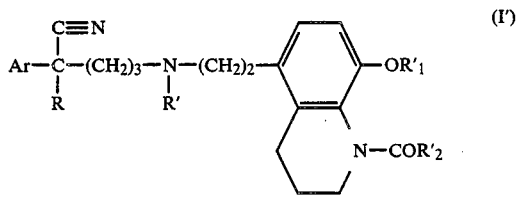
(I')

in which Ar, R, R', R'$_1$ and R'$_2$ have the meanings defined above, characterised in that:

the compound of the general formula VI:

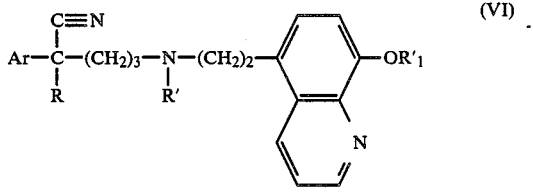
(VI)

in which Ar, R, R' and R'$_1$ have the meanings defined above, is hydrogenated, and the resulting compound of the general formula VII:

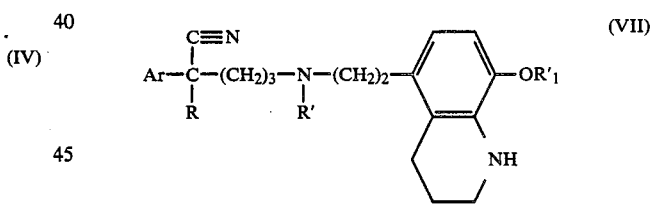
(VII)

in which Ar, R, R' and R'$_1$ are as defined above, is acylated with an acid chloride of the general formula VIII:

R'$_2$ CO Cl (VIII)

in which R'$_2$ has the meaning given above.

The compound (VI), which is simply the derivative of the general formula I in which Ar' represents:

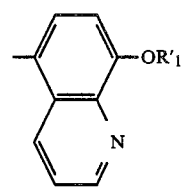

was prepared according to one of the two methods of preparation described above

It is particularly appropriate to hydrogenate the compound (VI) with hydrogen in the presence of nickel under a pressure of from 50 to 110 atmospheres, in an alcohol that has a low boiling point, at a temperature of approximately 90° C., or by means of a hydride, such as NaBH$_3$CN, in tetrahydrofuran at room temperature.

It is advantageous to carry out the acylation of the compound VII with R'$_2$COCl in tetrahydrofuran, in the presence of triethylamine, or, where R'$_2$ is hydrogen, with the mixture HCOOH 99% dimethylformamide.

The derivatives (I) prepared according to the processes described above may be purified either by flash chromatography on an SiO$_2$ column (230–400 mesh) under 0.5–0.8 bar N$_2$, using the systems AcOEt or CH$_2$Cl$_2$—MeOH (95-5) or benzene—MeOH (95-5), or by recrystallisation in the form of salts. The new compounds (I) thus obtained may be converted into addition salts with acids, these salts as such forming part of the present invention. As acids which may be employed for the formation of these salts there may be mentioned, for example, in the mineral series, hydrochloric, hydrobromic, sulphuric and phosphoric acids and, in the organic series, acetic, propionic, maleic, fumaric, tartaric, citric, oxalic, benzoic, methanesulphonic and isethionic acids.

The raw materials necessary for the preparation of the compounds I were themselves prepared according to the techniques described in the literature. Thus:

the compounds of the formula:

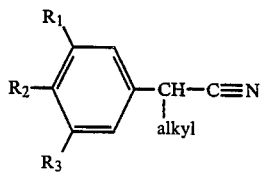

were prepared according to CARLSON et al. Helv. 46, 2271 (1983);

the compounds of the formula:

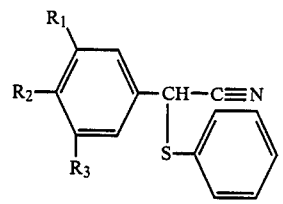

were prepared according to E. MARCHAND, G. MOREL and A. FOUCAUD—Synthesis (1978), 360–361, and purified by flash chromatography;

the compounds of the formula:

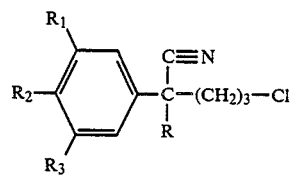

were prepared according to Belgium Patent No. 704,190 of Sept. 22nd 1967 (KNOLL), and purified in the form of oils by flash chromatography; and the compounds of the formula:

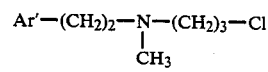

were prepared according to RAMUZ—Arzn. Forsch. 28 (II), 2049–2050, (1978), and purified by distillation under reduced pressure or by flash chromatography.

The characteristics of the raw materials of the formula:

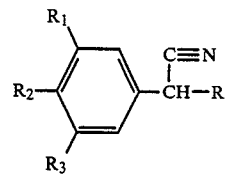

used for preparing the compounds which are the subject of the Examples described below are summarised in the following table:

CHARACTERISTICS OF THE COMPOUNDS OF THE FORMULA:

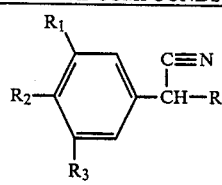

| REFERENCE COMPOUND | R$_1$ | R$_2$ | R$_3$ | R | PHYSICAL CONSTANT |
|---|---|---|---|---|---|
| a | —OCH$_3$ | H | H | —CH(CH$_3$)$_2$ | Bp/8 mmHg = 106–110° C. $n_{24}^D$ = 1.5135 |
| b | —OCH$_3$ | H | H | —(CH$_2$)$_{11}$—CH$_3$ | Bp/0.3 mmHg = 160–190° C. $n_{24}^D$ = 1.4910 |

-continued
CHARACTERISTICS OF THE COMPOUNDS OF THE FORMULA:

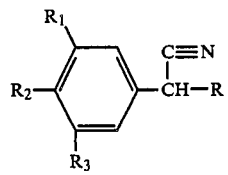

| REFERENCE COMPOUND | $R_1$ | $R_2$ | $R_3$ | R | PHYSICAL CONSTANT |
|---|---|---|---|---|---|
| c | —OCH₃ | H | H | —S—C₆H₅ | M.p. 82° C. |
| d | —CF₃ | H | H | —S—C₆H₅ | Oil |
| e | —OCH₃ | —OCH₃ | H | —S—C₆H₄—Cl | Oil |
| f | —OCH₃ | —OCH₃ | H | —S—C₆H₄—CH₃ | Oil |
| g* | —OCH₃ | —OCH₃ | H | —SO₂—C₆H₅ | M.p. 126° C. |
| h | H | —O—CH₂—O— | | —S—C₆H₅ | Oil |
| i | H | —O—CH=CH—O— | | —S—C₆H₅ | M.p. 72° C. |
| j | H | —O—CH=CH—O— | | —CH(CH₃)₂ | Oil |

*Derivative (g) was prepared by oxidation of the corresponding derivative in which R = 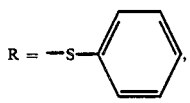, with pyridinium chlorochromate in CH₂Cl₂.

The characteristics of the raw materials (VI) used in the Examples described below are summarised in the following table:

CHARACTERISTICS OF THE COMPOUNDS OF THE FORMULA:

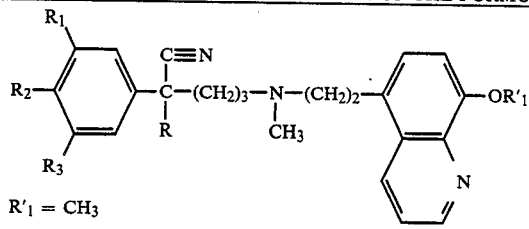

$R'_1 = CH_3$

| $R_1$ | $R_2$ | $R_3$ | R | ISOLATED FORM | M.p. |
|---|---|---|---|---|---|
| H | —OCH$_3$ | —OCH$_3$ | —CH(CH$_3$)$_2$ | dihydrochloride | 200° C. |
| H | O—CH=CH—O— | | —CH(CH$_3$)$_2$ | dihydrochloride | 202° C. |
| H | —OCH$_3$ | —OCH$_3$ | —SO$_2$—C$_6$H$_5$ | dihydrochloride | 188° C. |
| H | —OCH$_3$ | —OCH$_3$ | —S—C$_6$H$_5$ | base | Oil |
| H | O—CH=CH—O | | —S—C$_6$H$_5$ | base | Oil |
| —CF$_3$ | H | H | —S—C$_6$H$_5$ | base | Oil |
| H | —O—CH$_2$—O— | | —S—C$_6$H$_5$ | base | Oil |
| H | —OCH$_3$ | —OCH$_3$ | —S—C$_6$H$_4$—Cl | base | Oil |
| H | —OCH$_3$ | —OCH$_3$ | —S—C$_6$H$_4$—CH$_3$ | base | Oil |
| —OCH$_3$ | H | H | —CH(CH$_3$)$_2$ | base | Oil |
| —OCH$_3$ | H | H | —(CH$_2$)$_{11}$—CH$_3$ | base | Oil |
| —OCH$_3$ | H | H | —S—C$_6$H$_5$ | base | Oil |

The compounds of the general formula I and their physiologically tolerable salts have valuable pharmacological and therapeutic properties, especially properties of antagonism to intracellular movements of calcium.

A pharmacological study of compounds of the invention was carried out:
  in vitro by means of studies using isolated organs of rats, and regarding fixation with calmodulin, and
  in vivo, in dogs, in comparison with the properties of Verapamil, a well-known anti-calcium agent, which was used as the reference product.

The operating methods and the results obtained are the subject of the pharmacological examples included below.

Pharmacological tests in vitro have shown that these compounds are powerful modulators of intracellular and transmembrane movements of calcium. Certain cellular activities of smooth or striated muscles, especially their contractility, are associated with the intracytoplasmic concentration of calcium and it has been possible to demonstrate a disturbance of this concentration in certain disorders causing muscular contraction, especially angina, arterial hypertension, asthma, migraine and oesophagal spasms.

Calcium also plays a part in the regulation of cellular metabolism, especially mitochondrial metabolism, and this metabolism is disturbed in diseases such as cardiac or cerebral ischaemia.

The pharmacological properties of the derivatives of the invention therefore permit their use in the treatment of disorders requiring modulators of transmembrane and intracellular movements of calcium and, especially, in the treatment of hypertension, angina, asthma, oesophagal spasms, migraine, and myocardial and cerebral ischaemia.

The present invention also relates to pharmaceutical compositions containing, as active ingredient, a derivative of the general formula I or a physiologically tolerable salt thereof, in admixture or in conjunction with a suitable pharmaceutical carrier.

The pharmaceutical compositions thus obtained are advantageously presented in various forms, such as, for example, tablets, dragées, gelatine capsules, glossettes or galenical preparations suitable for sublingual administration, suppositories or injectable or drinkable solutions, and are to be administered orally, rectally or parenterally. The dosage may vary widely depending on the age and weight of the patient, the nature and severity of the disorder to be treated and also on the mode of administration. In human therapeutics, when administered intravenously or orally, generally the unit dose will range from 10 to 200 mg and the daily dose will range from 30 to 600 mg.

The following Examples, which are not intended to be limiting, illustrate the invention. Unless indicated otherwise, melting points are determined using a Kofler hot plate.

EXAMPLE 1

2-(3-methoxyphenyl)-2-phenylthio-5-{N-[(1-acetyl-8-methoxy-1,2,3,4-tetrahydroquinol-5-yl)ethyl]-N-methylamino}-pentanenitrile

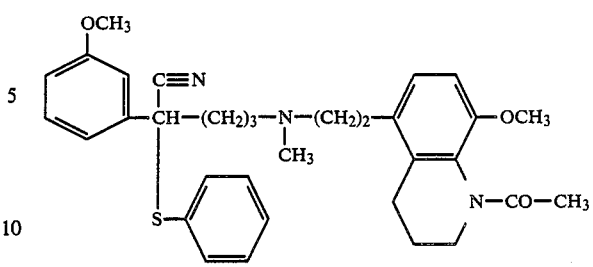

A solution of 3.3 g of 2-(3-methoxyphenyl)-2-phenylthio-5-chloropentanenitrile which melts at 50°–52° C. and 5 g of 1-acetyl-8-methoxy-5-(methyl-aminoethyl)-1,2,3,4-tetrahydroquinoline (oil) in 250 ml of acetonitrile is heated under reflux for 20 hours in the presence of 0.2 g of sodium iodide.

When the reaction is complete, the whole is cooled and the crystals of the hydrochloride of the starting amine are suction filtered and then the filtrate is evaporated to dryness. The residue is dissolved in ether and the solution is washed with water. After evaporation of the organic layer, the resulting oily base is converted into the fumarate in ethanol. 3 g of the fumarate of 2-(3-methoxyphenyl)-2-phenylthio-5-{N-[(1-acetyl-8-methoxy-1,2,3,4-tetrahydroquinol-5-yl)ethyl]-N-methyl-amino}-pentanenitrile are obtained in the form of an amorphous salt. The starting amine was prepared by debenzylation, with $H_2$-Pd(OH)$_2$ under 6 atm $H_2$, of 1-acetyl-8-methoxy-5-(N-methyl-N-benzylaminoethyl)-1,2,3,4-tetrahydroquinoline, which was itself prepared by acetylation by means of $CH_3COCl$-$(Et)_3N$ in tetrahydrofuran of 8-methoxy-5-(N-methyl-N-benzyl-aminoethyl)-tetrahydroguinoline, which was itself prepared by the action of N-methylbenzylamine on the hydrochloride of 8-methoxy-5-chloroethyl-1,2,3,4-tetrahydroquinoline in ethanol under reflux, which was itself prepared by chlorination, with an excess of $SOCl_2$, of the hydrochloride of the corresponding hydroxyethylated derivative, which was itself prepared by hydrogenation, with $H_2$/Ni under 100 atm, of 5-hydroxyethyl-8-methoxyquinoline which melts at 134° C.

2-(3-methoxyphenyl)-2-phenylthio-5-{N-[(1-acetyl-8-methoxy-1,2,3,4-tetrahydroqinol-5-yl)ethyl]-N-methylamino}-pentanenitrile was also prepared according to the process described in Example 2 below.

EXAMPLES 2 to 21

The following derivatives were prepared according to the methods described in Examples 1. 2. 2-(3,4-dimethoxyphenyl)-2-isopropyl-5-{N-[(8-methoxy-quinol-5-yl)ethyl]-N-methyl-amino}-pentanenitrile, m.p. of the dihydrochloride: 200° C. (anhydrous ethanol) 3. 2-(3,4-dimethoxyphenyl)-2-benzenesulphonyl-5-{N-[(8-methoxy-quinol-5-yl)ethyl]-N-methyl-amino}-pentanenitrile, m.p. of the dihydrochloride: 188° C. (anhydrous ethanol). 4. 2-(3,4-dimethoxyphenyl)-2-isopropyl-5-{N-[(1-acetyl-8-methoxy-1,2,3,4-tetrahydroquinol-5-yl)ethyl]-N-methyl-amino}-pentanenitrile, m.p. of the dihydrochloride: 198° C. (anhydrous ethanol). 5. 2-(benzodioxin-6-yl)-2-isopropyl-5-{N-[(1-acetyl-8-methoxy-1,2,3,4-tetrahydroqinol-5-yl)ethyl]-N-methyl-mino}-pentanenitrile. 6. 2-(3,4-dimethoxyphenyl)-2-phenylthio-5-{N-[(1-acetyl-8-methoxy-1,2,3,4-tetrahydroquinol-5-yl)ethyl]-N-methyl-amino}-pentanenitrile. 7. 2-(3,4-dimethoxyphenyl)-2-phenylthio-5-{N-[(1-acetyl-8-methoxy-1,2,3,4-tetrahydroquinol-5-yl)ethyl]- N-methyl-amino}-pentanenitrile. 8. 2-(benzodioxin-6-yl)-2-phenylthio-5-{N-[(1-acetyl-8-methoxy-1,2,3,4-tetrahydroqinol-5-yl)ethyl]-N-methyl-amino}-pentanenitrile. 9. 2-(3-trifluoromethylphenyl)-2-phenylthio-5-{N-[(1-acetyl-8-methoxy-1,2,3,4-tetrahydroquinol-5-yl)ethyl]- N-methyl-amino}-pentanenitrile. 10. 2-(3,4-methylenedioxyphenyl)-2-phenylthio-5-{N-[(1-acetyl-8-methoxy-1,2,3,4-tetrahydroquinol-5-yl)ethyl]-N-methyl-amino}-pentanenitrile. 11. 2-(3,4-dimethoxy-phenyl)-2-(p-chlorophenylthio)-5-{N-[(1-acetyl-8-methoxy-1,2,3,4-tetrahydroquinol-5-yl)ethyl]-N-methyl-amino}-pentanenitrile. 12. 2-(3,4-dimethoxyphenyl)-2-(p-methylphenylthio)- 5-{N-[(1-acetyl-8-methoxy-1,2,3,4-tetrahydroquinol-5-yl)ethyl]-N-methyl-amino}-pentanenitrile. 13. 2-(3-methoxyphenyl)-2-isopropyl-5-{N-[(1-acetyl-8-methoxy-1,2,3,4-tetrahydroquinol-5-yl)ethyl]-N-methyl-amino}-pentanenitrile. 14. 2-(3-methoxyphenyl)-2-phenylthio-5-[N-2-(3,4-dimethoxyphenethyl)-N-methyl-amino]-pentanenitrile, m.p. of the oxalate: 132° C. (anhydrous ethanol). 15. 2-(3-methoxyphenyl)-2-dodecanyl-5-{N-[(1-acetyl-8-methoxy-1,2,3,4-tetrahydroquinol-5-yl)ethyl]-N-methyl-amino}-pentanenitrile, m.p. of the acid oxalate: 115° C. (ethanol/ether). 16. 2-(3-methoxyphenyl)-2-phenylthio-5-{N-[(1-acetyl-8-methoxy-1,2,3,4-tetrahydroquinol-5-yl)ethyl]-N-ethyl-amino}-pentanenitrile. 17. 2-(3-methoxyphenyl)-2-phenylthio-5-{N-[(1-propionyl-8-methoxy-1,2,3,4-tetrahydroquinol-5-yl)-ethyl]-N-methyl-amino}-pentanenitrile, isolated in the form of fumarate. 18. 2-(3-methoxyphenyl)-2-phenylsulfonyl-5-{N-[(1-acetyl -8-methoxy-1,2,3,4-tetrahydroquinol-5-yl)-ethyl]-N-methyl -amino}-pentanenitrile, isolated in the form of fumarate.

EXAMPLE 19

2-(3-methoxyphenyl)-2-phenylthio-5-{N-[(1-acetyl-8-methoxy-1,2,3,4-tetrahydroquinol-5-yl)ethyl]-N-methyl-amino}-pentanenitrile.

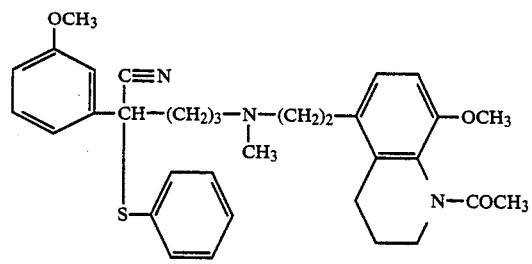

To a solution of 11.3 g of 2-(3-methoxyphenyl)-2-phenylthio-5-{N-methyl-N-[(8-methoxy-quinol-5-yl)ethyl]amino}-pentanenitrile (oil) prepared as in Example 1, in 500 ml of methanol there are added, under reflux, in 3 equal portions: 3×5.6 g of NaBH$_3$CN, each portion being followed over a period of 45 minutes by the addition of 3×89.3 ml of HCl to maintain the pH at 6–7.

After the third addition of acid, the whole is heated for a further 1½ hours and cooled, and the mixture is acidified with 35.7 ml of concentrated HCl. The whole is evaporated to dryness and extracted with CH$_2$Cl$_2$, washed with 10% CO$_3$Na$_2$ and with water, and dried over Na$_2$SO$_4$. 11.5 g of crude oily base are obtained and this is purified on 300 g of silica, eluting with the mixture ACOEt-CH$_2$Cl$_2$ (50—50) under 0.5 atm of N$_2$. After evaporation, 6.9 g of 2-(3- methoxyphenyl)-2-phenylthio-5-{N-methyl-N-[(8-methoxy-1,2,3,4-tetrahydroquinol-5-yl)-ethyl]amino}-pentanenitrile are obtained in the form of an oil.

This is dissolved in 150 ml of anhydrous tetrahydrofuran, 2.03 g of triethylamine are added, the solution is cooled to 5° C. and there is poured in at that temperature, within 15 minutes, a solution of 1.58 g of acetyl chloride in 30 ml of tetrahydrofuran. The whole is left at 5° C. for 1 hour and at room temperature for 1 hour, then the triethylamine hydrochloride is filtered off.

The whole is evaporated to dryness and 5.4 g of oil are obtained which are converted into the (amorphous) fumarate in ethanol.

The derivatives which are the subject of Examples 4, 5, 6, 7, 8, 9, 10, 11, 12, 13 and 15 to 16 were also prepared according to the process described in Example 19.

EXAMPLE 20

Pharmacological study in vitro

A. Methodology a. Study of isolated organs removed from rats

Male Wistar rats weighing from 350 to 400 g are used.

After rapid sacrifice of the animal, the following are removed:

the aorta, dissected and prepared in rings; after an equilibration period of 1 hour in the reference physiological solution (1), the prepared specimens are stimulated with a solution rich in potassium (K+) (100 mM) or with noradrenaline (NA) ($10^{-6}$M).

The substances to be tested are then added (test sample 0.2 ml) in cumulative doses every 15 minutes.

The relaxation values obtained permit an activity-dose curve to be constructed, enabling the IC$_{50}$ to be calculated in M.

the right auricle (RA) and left auricle (LA) RA beats spontaneously.

LA is stimulated electrically at a rate of 3 Hz (180 beats per min.) (amplitude of the stimulations: threshold ×2).

Stabilisation is obtained in physiological liquid (2) after 30 minutes.

The substances to be tested are then added (test sample 0.2 ml) in cumulative doses every 15 minutes. The effects on RA are chronotropic. The effects on LA are inotropic. The construction of the activity-dose curves enables the IC$_{50}$, expressed in M, to be measured.

The characteristics of the solutions used are as follows:

(1) Physiological solution (in mM): NaCl 112; KCl 5; KH$_2$PO$_4$ 1; MgSO$_4$ 1.2; CaCl$_2$ 2.5; NaHCO$_3$ 25; glucose 11.5.

Hyperpotassic solution: NaCl 17; KCl 100, etc. +95% O$_2$, 5% CO$_2$; pH 7.4 T°=37° C.

(2) Physiological solution (in mM): NaCl 118; KCl 4.7; CaCl$_2$ 2.6; MgCl$_2$ 1.2; NaH$_2$PO$_4$ 1; NaHCO$_3$ 25; glucose 11.1; +95% O$_2$, 5% CO$_2$; pH 7.4 T°=35° C.

b. Fixation on calcium calmodulin binding

The orientations of synthesis which may lead to possibilities of inhibiting calmodulin are evaluated by measuring the fluorescence of dansylated calmodulin.

The substances to be tested are added to the experimental vessel (2 ml). The increase in fluorescence of dansylated calmodulin enables effect-dose curves to be constructed; measuring the EC$_{50}$ gives an apparent Kd value. After extrapolation of the apparent Kd values to 0 calmodulin, the experiments carried out for different calcium-calmodulin concentration values enable the characteristic Kd values of the tested substances to be determined (Method proposed by Johnson and Wittenauer, 1983, Biochem., 211, 473–479).

c. Evaluation of myocardium/vessel selectivity

The $IC_{50}$ LA/$IC_{50}$ aorta ratio leads to a first evaluation; the high values indicate vascular selectivity.

d. Evaluation of the possibility of inhibition at the calmodulin level

When the Kd/$IC_{50}$ aorta ratio is close to 1, it indicates vascular inhibition through this mechanism; this concept may also be supported by a relatively low $IC_{50}$ value obtained on the aorta by noradrenergic stimulation.

e. Moreover, the aorta artery of the rat without endothelium may be stimulated by an increase of intracellular calcium of the smooth fiber through ionophore calcium A 23187 at a concentration of $5.10^{-6}M$. This contraction may be inhibited by some molecules acting on intracellular mecanisms. Verapamil is inactive on this phenomenon. The product of Example 1 is active with an IC50 of about $10^{-6}M$. This effect may be put together with the observations about calmodulin binding.

B. Results

The results obtained with products illustrating the invention are listed in the table below.

These effects are of the same order of magnitude as those obtained with Verapamil; however, these new molecules exhibit a greater vascular selectivity than that shown by Verapamil, and this selectivity is greatest with the product of Example 1. Moreover, the pharmacological effects of the products of Examples 1 and 7 indicate intracellular inhibitory mechanisms and, especially, a calcium-calmodulin inhibition mechanism.

EXAMPLE 21

Pharmacological study in vivo

A. Methodology

A haemodynamic study was carried out on mongrel dogs weighing from 25 to 30 kg, which were anaesthetised with sodium pentobarbital in a dose of 30 mg/kg i.v., intubated and ventilated, and subjected to a thoracotomy at the 5th left intercostal space.

The average coronary flow is measured by means of a Gould SP 2202 electromagnetic flow meter, the electromagnetic ring being positioned at the level of the circumflex branch of the left coronary artery. The left and aortal ventricular pressures are measured by means of MILLAR probes introduced by the femoral artery route. The cardiac frequency is measured by Biotach Gould ECG (derivation D2); the gases of the aortal

| PRODUCTS | AORTA St:$K^+$ | AORTA St:NA | RIGHT AURICLE (RA) (CHRONOTROPIC EFFECT) | LEFT AURICLE (LA) (INOTROPIC EFFECT) | LA/AORTA SELECTIVITY (St:$K^+$) | Kd (cam) | Kd/$IC_{50}$ AORTA $K^+$ |
|---|---|---|---|---|---|---|---|
| EXAMPLE 1 | $7.5 \times 10^{-7}$ | $5.5 \times 10^{-6}$ | $10^{-5}$ | $8.2 \times 10^{-5}$ | 100 | $8.1 \times 10^{-7}$ | 1.08 |
|  | $6 \times 10^{-7}$ | $1 \times 10^{-5}$ | $5 \times 10^{-5}$ | $7.4 \times 10^{-6}$ | 12 | $6.5 \times 10^{-5}$ | 10.8 |
| EXAMPLE 4 | $6 \times 10^{-7}$ | $1.3 \times 10^{-5}$ | $1.5 \times 10^{-6}$ | $8 \times 10^{-5}$ | 13 | $6.5 \times 10^{-6}$ | 10.8 |
| EXAMPLE 7 | $3.6 \times 10^{-7}$ | $3 \times 10^{-6}$ | $2.9 \times 10^{-6}$ | $5.5 \times 10^{-6}$ | 15 | $2.4 \times 10^{-6}$ | 0.66 |
| EXAMPLE 13 | $2.5 \times 10^{-7}$ | $3 \times 10^{-5}$ | $10^{-6}$ | $5.2 \times 10^{-6}$ | 20 | $3.4 \times 10^{-5}$ | 97 |
| REFERENCE VERAPAMIL | $8 \times 10^{-7}$ | $1.4 \times 10^{-5}$ | $2 \times 10^{-6}$ | $2 \times 10^{-6}$ | 5.6 | $4.5 \times 10^{-5}$ | 195 |

C. Binding on $Ca^{++}$ channels of membranes of transverse tubules in skeletal muscle.

The measurement of the affinity constants for the $Ca^{++}$ channel shows an exceptional value of Kd of 1 nM for the product of Example 1 while it is of 20 nM for verapamil, on the same preparation.

D. Conclusions of the study in vitro

The molecules presented lead to vascular relaxations and to negative inotropic and chronotropic effects.

blood and of the coronary sinus are analysed by an ABL3 radiometer.

The products tested were injected by the femoral vein route.

B. Results

The results of the haemodynamic study carried out on a certain number of representative products of the invention and one reference product (Verapamil) are summarised in the table below.

| | MAXIMUM VARIATIONS EXPRESSED AS DELTA % WHATEVER THE TIME (EXCEPT FOR dP/dt MEASURED AT 20 MINUTES) | | | | | | | |
|---|---|---|---|---|---|---|---|---|
| PRODUCT | DOSE μg/kg* IV | CF | AAP | ACF | $PO_2SC$ | I/C | dP/dt | PR |
| EXAMPLE 1 | 30 | −5 | 0 | +54 | +14 | +19 | | 0 |
| EXAMPLE 1 | 100 | −10 | −9 | +109 | +36 | +55 | 0 | +7 |
| EXAMPLE 1 | 300 | −14 | −24 | +117 | +63 | +118 | −3 | +19 |
| EXAMPLE 4 | 300 | −17 | −14 | +84 | +47 | +83 | −2 | +27 |
| EXAMPLE 7 | 300 | −7 | −16 | +77 | +36 | +52 | 0 | +15 |
| EXAMPLE 7 | 1000 | −11 | −36 | +132 | +49 | +107 | −3 | +37 |
| EXAMPLE 13 | 100 | −11 | −10 | +42 | +40 | +45 | 0 | +10 |
| EXAMPLE 13 | 300 | −15 | −23 | +84 | +59 | +99 | −6 | +32 |
| VERAPAMIL | 30 | −4 | −5 | +32 | +18 | +18 | | +6 |
| VERAPAMIL | 100 | −9 | −16 | +87 | +42 | +60 | −5 | +14 |

-continued

| | MAXIMUM VARIATIONS EXPRESSED AS DELTA % WHATEVER THE TIME (EXCEPT FOR dP/dt MEASURED AT 20 MINUTES) | | | | | | | |
|---|---|---|---|---|---|---|---|---|
| PRODUCT | DOSE μg/kg* IV | CF | AAP | ACF | PO₂SC | I/C | dP/dt | PR |
| VERAPAMIL | 300 | −8 | −21 | +99 | +71 | +127 | −13 | +40 |

Doses are expressed as a quantity of the product in the form of a base.
CF: Cardiac frequency
AAP: Average arterial pressure
ACF: Average coronary flow
PO₂SC: PO₂ coronary blood sinus
I/C: Myocardial O₂ intake/consumption ratio
dP/dt: Left ventricular pressure derivative
PR: PR space of the ECG C. Conclusion of the study in vivo The haemodynamic measurements carried out on dogs show that the products of the invention which were tested have properties that are at least equivalent to those of the reference substance (Verapamil): however, for two of these products, those of Examples 1 and 7, the cardiotropic effect is lower, which is expressed, especially, by the absence of a negative inotropic effect and by the reduction in the percentage increase in the PR duration.

These data confirm, in animals, the observations made on isolated organs. They confirm the originality of the products of the invention compared with Verapamil.

We claim:

1. A compound selected from the group consisting of:
a 5-aminopentanenitrile compound of the formula:

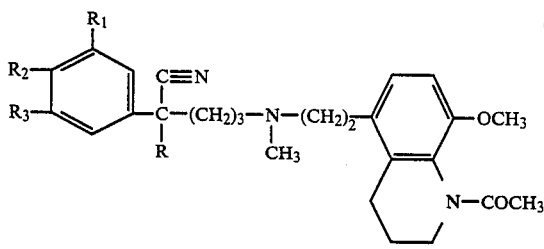

(I)

in which:

R₁ is selected from the group consisting of hydrogen, trifluoromethyl, and methoxy;

R₂ and R₃, which are the same or different, are each selected from the group consisting of hydrogen and methoxy, or R₂ and R₃ together represent a radical selected from the group consisting of —O—CH=CH—O— and —O—CH₂—O—;

R is selected from the group consisting of straight-chain and branched alkyl containing 3 to 15 carbon atoms, inclusive, and a radical of the formula:

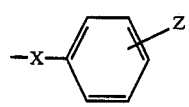

in which:

X is selected from the group consisting of S and SO₂ and Z is selected from the group consisting of hydrogen and methyl;

and physiologically-tolerable acid addition salts thereof.

2. A compound of claim 1 selected from the group consisting of:
a 5-aminopentanenitrile compound of the formula I':

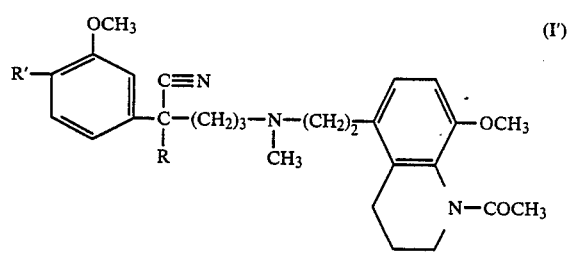

(I')

in which:

R' is selected from the group consisting of hydrogen and methoxy, and

R is selected from the group consisting of isopropyl and

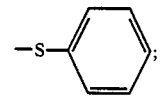

and physiologically-tolerable acid addition salts thereof.

3. A compound of claim 1 which is:
2-(3-methoxyphenyl)-2-phenylthio-5-{N-[(1-acetyl-8-methoxy-1,2,3,4-tetrahydroquinol-5-yl)ethyl]-N-methyl-amino}-pentanenitrile.

4. A compound of claim 1 which is:
2-(3,4-dimethoxyphenyl)-2-isopropyl-5-{N-[(1-acetyl-8-methoxy-1,2,3,4-tetrahydroquinol-5-yl)ethyl]-N-methyl-amino}-pentanenitrile.

5. A compound of claim 1 which is:
2-(3,4-dimethoxyphenyl)-2-phenylthio-5-{N-[(1-acetyl-8-methoxy-1,2,3,4-tetrahydroquinol-5-yl)ethyl]-N-methyl-amino}-pentanenitrile.

6. A compound of claim 1 which is:
2-(3-methoxyphenyl)-2-isopropyl-5-{N-[(1-acetyl-8-methoxy-1,2,3,4-tetrahydroquinol-5-yl)ethyl]-N-methyl-amino}-pentanenitrile.

7. Pharmaceutical compositions containing as active ingredient a compound of claim 1 together with a suitable pharmaceutical carrier.

8. A method for treating a living animal body afflicted with disorders requiring modulators of transmembrane and intracellular movements of calcium comprising the step of administering to the said living animal an amount of a compound of claim 1 which is effective for the alleviation of the said condition.

* * * * *

UNITED STATES PATENT AND TRADEMARK OFFICE
CERTIFICATE OF CORRECTION

PATENT NO. : 4,792,559

DATED : December 20, 1988

INVENTOR(S) : Gilbert Regnier, Yves-Michel Gargouil and Jean-Paul Vilaine

It is certified that error appears in the above-identified patent and that said Letters Patent is hereby corrected as shown below:

Col. 5, line 24; delete the period "." after "and"

Col. 12, line 36; "-tetrahydroguinoline," should read -- -tetrahydroquinoline, --

Col. 12, line 46; "-tetrahydroqinol-" should read -- -tetrahydroquinol- --

Col. 12, line 64; "-tetrahydroqinol-" should read -- -tetrahydroquinol- --

Col. 13, lines 11 and 14; change "2-(p-" to read -- 2-(p- -- in both occurrences Cols. 15&16, in first Table; delete the line after "EXAMPLE 1" line Signed and Sealed this Twenty-sixth Day of September, 1989

Attest:

DONALD J. QUIGG

Attesting Officer

Commissioner of Patents and Trademarks